United States Patent [19]

Gershony et al.

[11] Patent Number: 5,383,896
[45] Date of Patent: Jan. 24, 1995

[54] VASCULAR SEALING DEVICE

[76] Inventors: Gary Gershony, 1599 Swan Dr., Tulsa, Okla. 74120; Karol W. Nowakowski, 5476 Landmark Cir., Moundview, Minn. 55112

[21] Appl. No.: 67,213

[22] Filed: May 25, 1993

[51] Int. Cl.⁶ .............................................. A61B 17/12
[52] U.S. Cl. .................................... 606/213; 606/194; 604/53; 604/96; 604/178
[58] Field of Search ............... 606/192, 194, 213, 215, 606/232; 604/49, 51–53, 96, 178, 256

[56] References Cited

U.S. PATENT DOCUMENTS

| | | | |
|---|---|---|---|
| 2,862,497 | 12/1958 | Pagano | 604/256 |
| 4,555,242 | 11/1985 | Saudagar | 606/192 |
| 4,701,163 | 10/1987 | Parks | 604/178 |
| 4,738,658 | 4/1988 | Magro et al. | 604/53 |
| 4,852,568 | 8/1989 | Kensey | |
| 4,890,612 | 2/1990 | Kensey | 606/213 |
| 5,021,059 | 6/1991 | Kensey et al. | 606/213 |
| 5,042,985 | 8/1991 | Elliot et al. | 606/192 |
| 5,053,046 | 10/1991 | Janese | 606/215 |
| 5,061,274 | 10/1991 | Kensey | 606/213 |
| 5,108,421 | 4/1992 | Fowler | 606/213 |
| 5,129,882 | 7/1992 | Weldon et al. | 606/213 |
| 5,159,937 | 11/1992 | Tremulis | 606/194 |
| 5,176,692 | 1/1993 | Wilk et al. | 606/213 |
| 5,222,974 | 6/1993 | Kensey et al. | 606/213 |
| 5,250,025 | 10/1993 | Sosnowski et al. | 604/51 |

FOREIGN PATENT DOCUMENTS

| | | | |
|---|---|---|---|
| 416734 | 3/1991 | European Pat. Off. | |
| 90/14796 | 12/1990 | WIPO | 606/213 |
| 92/22252 | 12/1992 | WIPO | 606/213 |

Primary Examiner—Ralph A. Lewis
Attorney, Agent, or Firm—Joel Skinner

[57] ABSTRACT

A device for sealing an opening or puncture in the wall of a blood vessel or other percutaneous openings. The device includes a shaft section of a small diameter, with an expandable balloon and atraumatic tip at its distal end. The proximal end of the device has an inflation/deflation port which is utilized to inflate the balloon once it is in place within the blood vessel or other body cavity. The entire device is typically placed through a vascular sheath, which is used during invasive percutaneous vascular procedures. The balloon is inflated and withdrawn until it engages the inner surface of the blood vessel or body cavity. The sheath is withdrawn from within the blood vessel or other body cavity to the outside of the body. A fixation collar loaded onto the shaft of the device allows for securement in place, within the blood vessel or other body cavity.

16 Claims, 3 Drawing Sheets

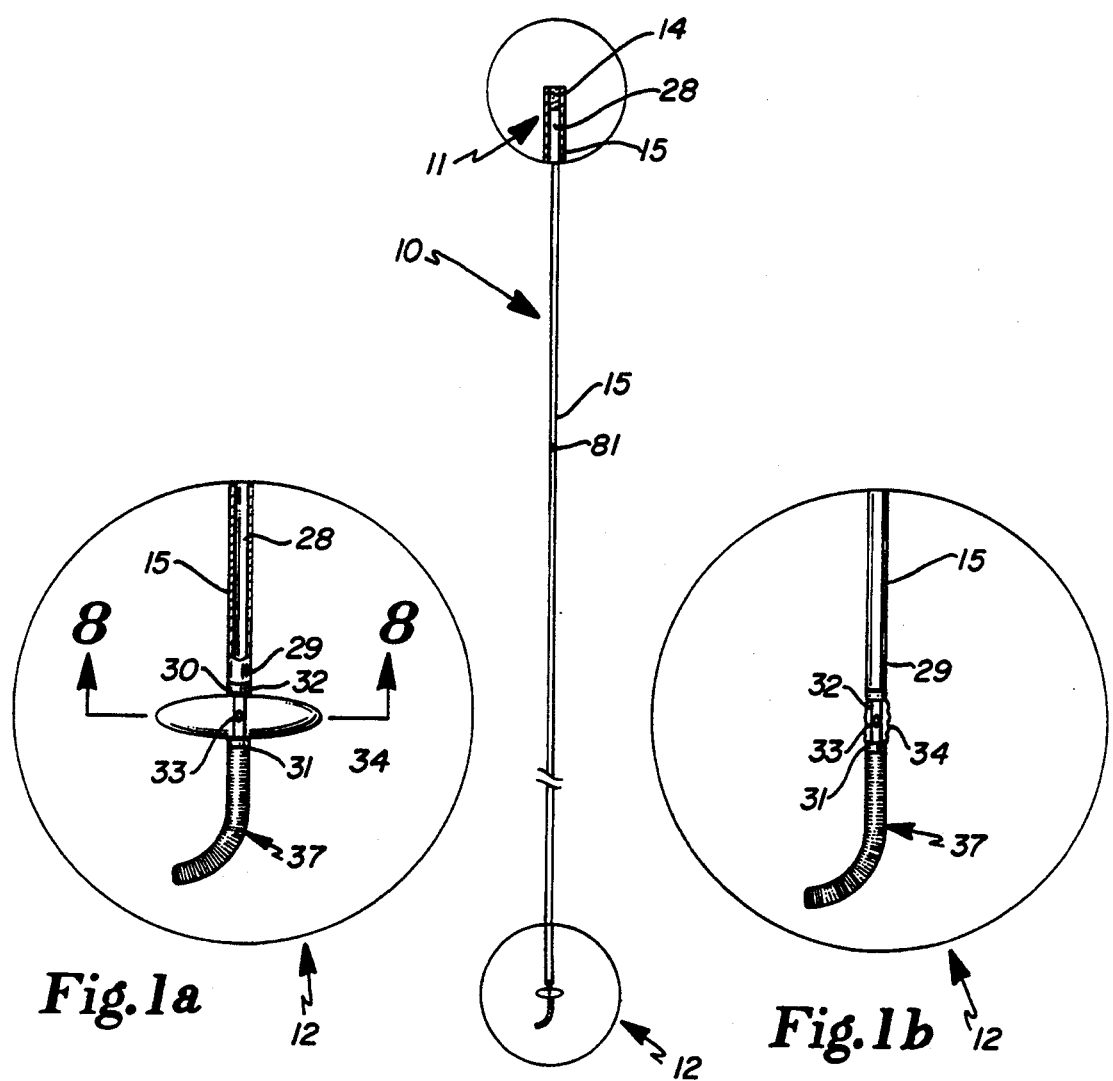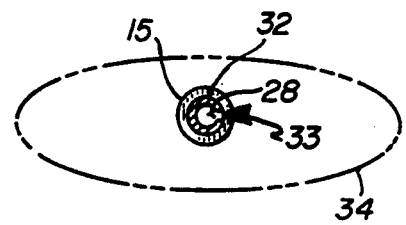

VASCULAR SEALING DEVICE

BACKGROUND OF THE INVENTION

1. Field of the Invention

This invention relates to medical devices in general and, more particularly, to hemostatic devices. The device is particularly useful for arresting the flow of blood or hemorrhage from punctures of the vascular system.

2. Background Art

Various surgical procedures are performed by medical specialists such as cardiologists, utilizing percutaneous entry into a blood vessel or body cavity. Examples of such procedures include different techniques to recanalize atherosclerotic blood vessels, such as balloon angioplasty or atherectomy. Recently, both the types and number of procedures performed utilizing the above mentioned percutaneous access to blood vessels have increased greatly.

These procedures generally involve the percutaneous puncture with a thin walled needle into a blood vessel. Following this, a guidewire is placed through the needle into the blood vessel and the needle is withdrawn. An intravascular sheath of variable size is then advanced over the guidewire, percutaneously, into the lumen of the blood vessel. The introducer sheath is then used as an ingress/egress means during the procedure. Following completion of the procedure, the introducer sheath may be removed, but this requires the application of prolonged manual pressure over the puncture site by a physician or other suitably trained medical personnel. The time involved here is frequently extensive since patients are often treated with a variety of anticoagulant and thrombolytic agents, particularly in the setting of a heart attack. Alternatively, the sheath may be left in the puncture site for a prolonged period of time until the patient's coagulation status has returned to normal. Depending on the size of the vascular sheath, there may be an increased risk of bleeding to the patient, which may require blood transfusion. In addition, there is a significant risk for injury to the blood vessel upon removal of the sheath, particularly if the sheath has been in place for a prolonged period of time. This includes the possible development of an pseudoaneurysm or severe hematoma. The current technique for removal of introducer sheaths is also painful to the patient and requires prolonged bed rest after removal. This adds to the discomfort for the patient, as well as prolonging hospitalization and costs.

Many of the intra-vascular procedures are performed in patients who are clinically unstable or who have the potential to become so, following completion of the procedure. Following removal of the vascular access sheath, it could be cumbersome and sometimes difficult to re-enter the blood vessel if necessary. Thus, with the current technique for removal of the sheath following the procedure, no easy, reliable method is available to allow reaccess to the lumen of the blood vessel, if necessary.

In the past, various devices and methods have been used and proposed in an attempt to seal punctures in blood vessels by injection of a resorbable hemostatic plug into the puncture site. U.S. Pat. No. 4,744,364 (Kensey), U.S. Pat. No. 4,852,568 (Kensey), and U.S. Pat. No. 4,890,612 (Kensey) disclose such a method and device. These prior art devices and methods have a number of shortcomings and problems. Specifically, they involve injection of a foreign pharmacologic material into the vasculature to induce hemostasis. Once the prior art device is employed, it cannot be removed without surgical intervention and, if it has not been placed correctly or has been injected into the vascular lumen, it could cause complications such as vascular occlusion. The prior art devices do not provide the capability of reentry into the blood vessel lumen, when necessary, if a change occurs in the patient's clinical status. The prior art does not teach the use of simple nonsurgical means for effecting the closure of a puncture in a blood vessel by using an expandable balloon to plug the opening, and without requiring sutures or the application of prolonged manual pressure.

Despite the need for a device and method in the art which overcomes the limitations and problems of the prior art, none insofar as is known has been proposed or developed. The present invention is specifically directed to overcoming all of the problems previously enumerated regarding the performance of invasive vascular procedures through a percutaneously placed sheath.

SUMMARY OF THE INVENTION

This invention provides a device for sealing an opening or puncture in the wall of a blood vessel. The device includes a shaft section of small diameter, with an expandable balloon and guidewire tip at its distal end. A fixation collar loaded onto the shaft of the device allows for securing of the sealing device in place, within the blood vessel or other body cavity. The proximal end of the device has a low profile port which is utilized to inflate and deflate the distal balloon once it is in place within the blood vessel.

The entire device is placed through a vascular introducer sheath of the type which is typically used during invasive percutaneous vascular procedures. The distal balloon is inflated and withdrawn until the balloon hemostatically engages the inner surface of the blood vessel. The sheath is withdrawn from within the blood vessel to the outside of the body. The introducer sheath is further preferably a "peel-away" type device. The fixation collar is preferably side loaded onto the shaft of the device and advanced until it is in contact with the skin surface, and tension is placed on the balloon within the blood vessel to secure it in contact with the inner surface of the puncture site.

These and other benefits of this invention will become clear from the following description by reference to the drawings.

BRIEF DESCRIPTION OF THE DRAWINGS

FIG. 1 is a perspective view of a vascular sealing device of the present invention, with segments enlarged to show details of the distal and proximal ends thereof.

FIG. 8 is a crossectional view of the vascular sealing device taken along line 8—8 of FIG. 1.

DESCRIPTION OF THE PREFERRED EMBODIMENT

Figure 2:
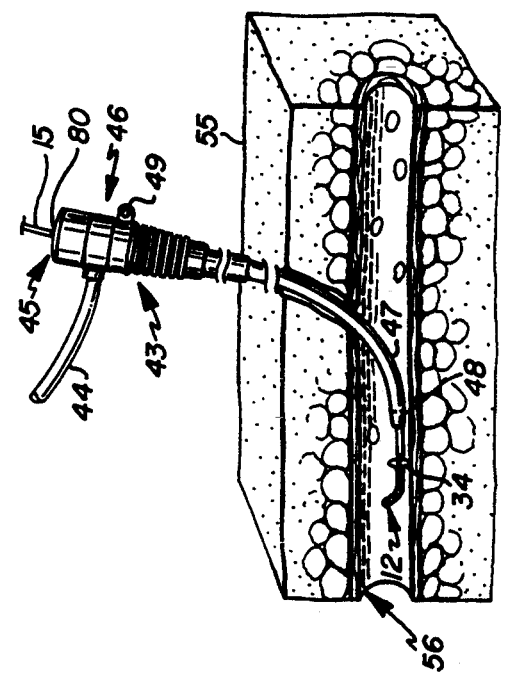
FIG. 2 is a view of the vascular sealing device inserted through an introducer sheath and into a patient's vascular system, which is shown enlarged and in section.
Figure 4:
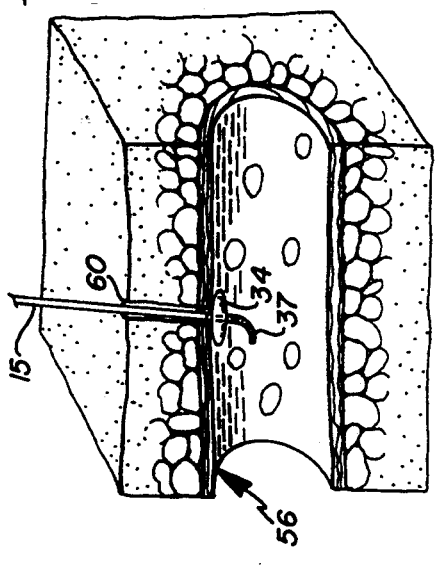
FIG. 4 is a view of the vascular sealing device with its balloon portion inflated, and further showing removal of the vascular sheath.

Referring to FIG. 1, a preferred form is shown of the vascular sealing device 10 for effecting closure of a puncture or other opening in a blood vessel, or other body cavity, which has been entered through percutaneous techniques. The device 10 is useable with a standard percutaneous vascular sheath or introducer. The vascular sealing device 10 is shown to have an elongated thin, generally tubular body or conduit 15 with proximal and distal ends 11 and 12, respectively. Basically, the proximal end 11 of the device 10 is for physician manipulation and connection to associated medical apparatus described further below, while the distal end 12 is for insertion into the patient's body. Located at the proximal end 11 of device 10 is an inflation/deflation port 14.

The body member 15 has a tubular structure constructed of hypotubing or a similar material. This structure also has a cylindrical and thin outer body wall with a central, continuous, and longitudinally extending lumen 28. The body member 15 has an outside diameter preferably not greater than 0.038 inches (0.965 mm.). The body 15 is semi-flexible and, importantly, has a predetermined rigidity such that central lumen 28 integrity is maintained. This is particularly important during longitudinal translational manipulation by the physician, through vascular introducer means (described below), into a percutaneous puncture in the patient's skin. The hypotubing of the body 15 is preferably constructed of a metallic material such as stainless steel, for example. Alternatively, the body 15 may be constructed of a polymeric material. The body member 15 is shown to have a length preferably of at least 11.79 inches (30 cm).

The proximal end 11 of the lumen or hollow interior 28 is sealed with elastomeric material, preferably silicone, to form an inflation/deflation port 14. The seal forms the inflation/deflation port 14 by adhering to the internal wall surfaces of the proximal end 11 of body 15. The seal is of sufficient strength to maintain a pressure difference between the internal lumen 28 and the proximally disposed exterior of the seal. This pressure difference is of a magnitude sufficient to maintain inflation of the balloon 34, which is in continuity with the lumen 28. The inflation/deflation port 14 is utilized by piercing its proximal face, preferably with a syringe needle, to a depth which allows the needle lumen to be in continuity with the lumen 28. An external syringe, attached to the proximal end of the needle, provides a piston means by which a gas or liquid is pumped into the balloon 34 for inflation, or out of the balloon 34 for deflation. Removal of the needle from the inflation/deflation port 14 causes the seal to re-establish the pressure differential barrier.

The structure of the proximal end 11 also allows the user to later slide a standard vascular sheath over the device body 15 and then to advance it to the puncture site for positioning within the blood vessel lumen. This allows reentry into the blood vessel, if necessary, for a further interventional procedure.

The bottom or distal end 12 of the device body 15 is shown to have a distal tip 29. The distal tip 29 further has an inset segment 32. The inset segment 32 has a tubular configuration and is oriented coaxially with respect to the distal tip 29. The inset segment 32 preferably has a diameter which is less than that of the distal tip 29 and a length equivalent to that of the wall of the balloon 34 when deflated. Thus, an inset with respect to the distal tip 29 is formed by this structure. The lumen 28 extends into the inset segment 32 and is communicatively connected to an orifice 33, which is disposed in the side wall of the inset segment 32. The orifice 33 is shown to have a circular configuration.

As is best shown in FIG. 1, exploded portions A and B, the balloon 34 is disposed about the inset segment 32. In an uninflated state, the balloon 34 has a tubular configuration and is sealingly secured at each of its ends to respective ends 30 and 31 of the inset segment 32. Sealing securement may be made by various methods, including adhesives, ultrasonic welding, and compression fitting. The uninflated diameter of the balloon 34 is such that it is disposed substantially within the recess space formed by the difference in diameter of the inset segment 32 and the distal tip 29. This provides a low profile device diameter which reduces vascular trauma and puncture site diameter upon removal. In an inflated state the balloon 34 preferably assumes a rounded configuration, for example elliptical, with a minimum inflated diameter of two times the french size of the introducer sheath puncture hole being sealed. In addition, the height or thickness of the inflated balloon 34 is preferably less than one half the diameter of a typical blood vessel being sealed, so as to minimize obstruction of flow through the blood vessel. The balloon 34 is preferably constructed of an expandable material such as natural latex.

A flexible atraumatic extension 37 is shown disposed at the distal end 12 of the vascular sealing device 10, extending from the inset segment 32. The extension 37 preferably has a tubular structure with a diameter equivalent to that of the distal tip 29. Importantly, the extension 37 is formed of a flexible material such as guidewire as known in the art. The extension 37 is shown to have an end portion which is preferably curved in its inoperative state. This structure decreases the level of trauma to the vessel wall during insertion and manipulation of the device 10.

Figure 3:
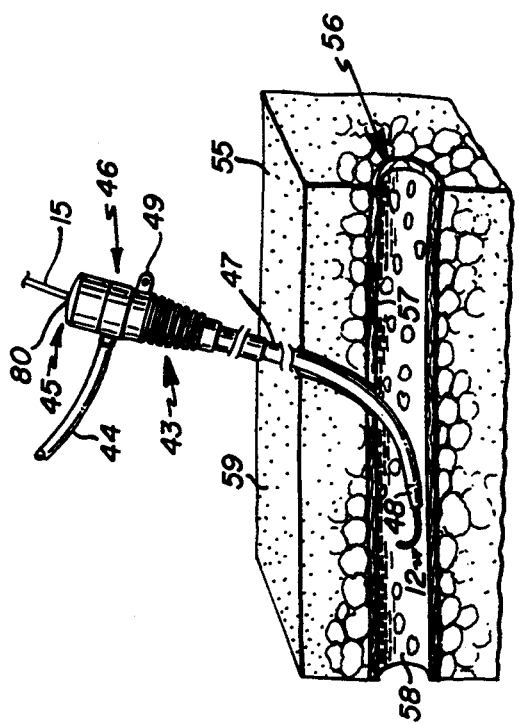
FIG. 3 is a view of the vascular sealing device inserted through a vascular sheath, and being inflated.
Figure 5:
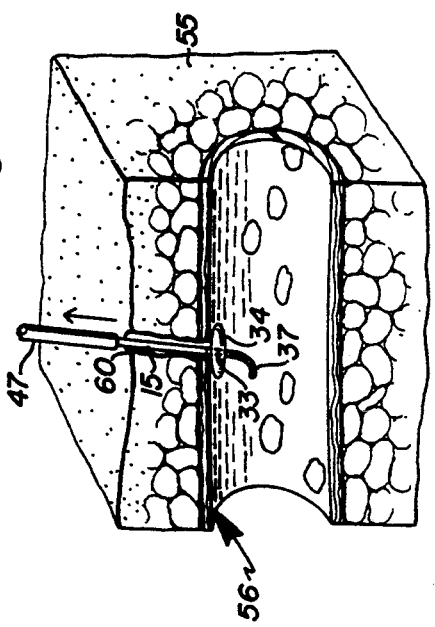
FIG. 5 is a view of the vascular sealing device with the balloon inflated and being pulled firmly up against the inner surface of a vascular puncture.

Referring to FIG. 1, 81 refers to a distance marker upon body 15 for the purpose of indicating to the user that the balloon 34 is distal to the sheath taper end 48 shown in FIGS. 2 and 3. By alignment of marker 81 at the top of the hemostatic valve opening at cap 45, proper location of the balloon 34 with respect to sheath tapered end 48 is assured.

Referring generally to FIGS. 2-7, in use, the vascular sealing device 10 is inserted into the input end 45 of an introducer or vascular sheath device 43 which has been previously positioned within the lumen 58 of a blood vessel 56. The typical introducer 43, as is well known, comprises a body structure 46, an elongated sheath 47 with a tapered end 48, a hemostatic ingress/egress valve 80 within a cap 45, an auxiliary tube 44 and a suture connector 49 which may be used to maintain the introducer 43 in an operative position on the patient's skin surface 55 for prolonged periods of time and to thereby permit reaccess to the patients vascular system 56. The body 46 of the introducer 43 remains on the exterior of the patient's body at all times, while the sheath 47 extends through puncture 60 in the skin surface 55, tissue 59, and vessel wall 57.

The vascular sealing device 10 is first inserted through the valve or gasket 80 of the introducer 43, distal end 12 first, and is advanced by physician manipulation of the body member 15, primarily, until the distal end 12 extends just beyond the distal tapered tip 48 of the sheath 47. Next, an inflator such as a syringe (not shown) pierces the inflation/deflation port 14 of device 10. Fluid or gas is advanced into the device 10 until a predetermined amount of balloon 34 inflation is attained. Then, the inflating means is removed. Next, the inflated balloon section 34 is pulled up against the vessel wall 56 at the puncture site 60, by manipulating the body member 15. At this point in the procedure, a hemostatic seal is effected at the puncture site 60. Next, the introducer sheath 47 is withdrawn by manipulation of the introducer body 46 and sheath 47 proximal end. The balloon section 34 remains abutted against the inner intraluminal surface 56 of the puncture site 60.

Figure 6:
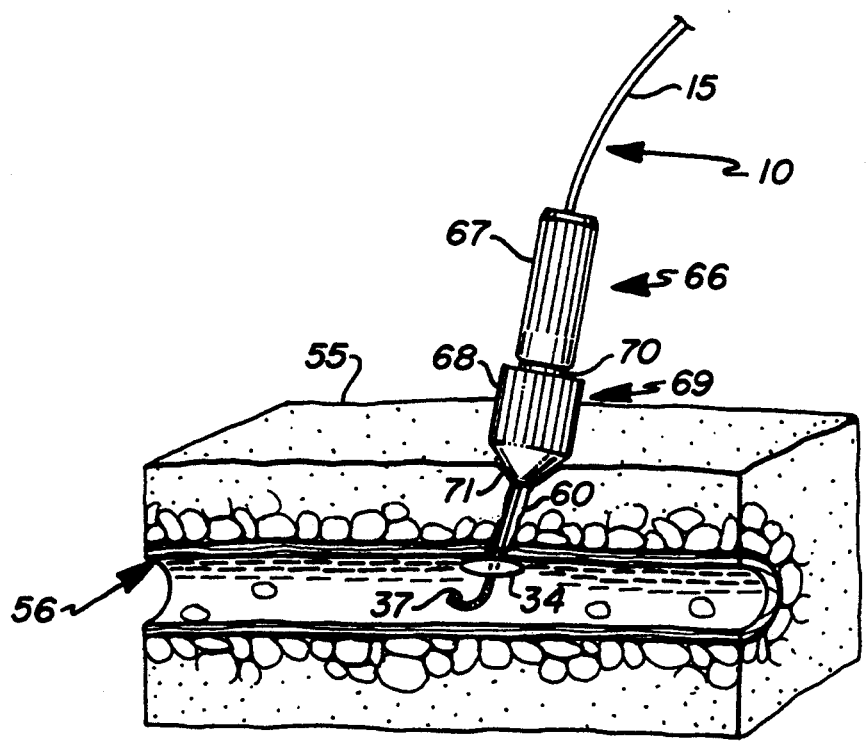
FIG. 6 is a view of the vascular sealing device with the balloon inflated and pulled taut against the inner surface of the vessel wall, and with placement of the external fixation device against the patient's skin surface.
Figure 7:
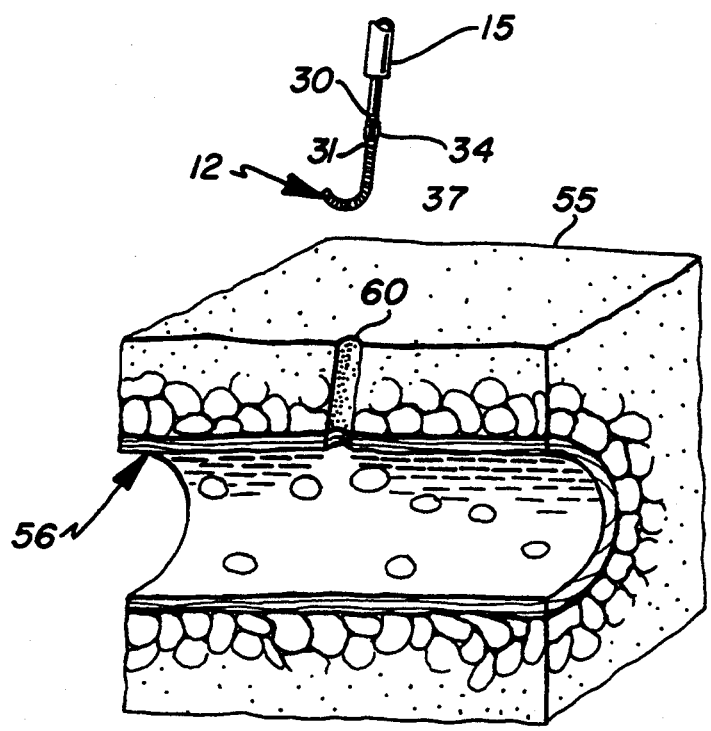
FIG. 7 is a view of the vascular sealing device with the balloon deflated and being removed from the blood vessel.

Referring to FIG. 6, the vascular sealing device 10 further comprises a fixation member 66 to hold it in an operative hemostatic orientation for a prolonged period of time. The fixation member 66 typically comprises a top member 67 and a bottom member 68 which interface at point 70. Preferably, the fixation member 66 has a side loading longitudinal channel 69. Also, the bottom member 68 has a surface which contacts the patient's skin surface 55. The fixation member 66 applies tension to the balloon 34, stabilizing it against the puncture site 60. Referring to FIG. 7, after a medically sufficient time period, for example upon an improvement in the patient's coagulation status following the intravascular medical procedure, the balloon 34 is deflated by again piercing the inflation/deflation port 14. The fixation member 66 is removed, and the remainder of the vascular sealing device 10 is removed from the puncture site 60. A small residual lumen remains. At this point, the use of normal compressive techniques will effect a complete closure of the puncture site 60. Due to the extremely low diameter of the device 10, a shortened period of manual compression is necessary to achieve hemostasis at the puncture site 60.

As many changes are possible to the embodiments of this invention utilizing the teachings thereof, the descriptions above, and the accompanying drawings should be interpreted in the illustrative and not the limited sense.

That which is claimed is:

1. A medical sealing apparatus for closing of an aperture in a patient body, comprising:
   a. a thin, elongated conduit having a central lumen, said conduit having proximal and distal ends, said conduit distal end being insertable into the patient body aperture and having an inflation segment including an external orifice which is communicatively connected to said lumen, said conduit proximal end having a cylindrical configuration of a uniform outside diameter;
   b. an expandable member sealingly disposed at said conduit distal end inflation segment, said expandable member being inflatable to a predetermined diameter;
   c. a seal consisting of an elastomeric material continuously and adheringly disposed in said conduit central lumen along a predetermined segment at said proximal end thereof, said seal permitting ingress and egress of fluid to and from said conduit lumen via a syringe; and
   d. a fixation member having a base portion for contact with the patient body and means to engage said conduit until the patient body aperture is closed.

2. The medical sealing device of claim 1, wherein said conduit has a predetermined outside diameter and length and is constructed of a metallic material having a predetermined degree of rigidity.

3. The medical sealing device of claim 2, wherein said conduit comprises hypotubing.

4. The medical sealing device of claim 1, wherein said conduit has a predetermined outside diameter and length and is constructed of a polymeric material having a predetermined degree of rigidity.

5. The medical sealing device of claim 1, wherein said inflation segment is a hollow tubular structure extending coaxially from said conduit distal end and having a predetermined outside diameter which is not greater than the diameter of said conduit at said distal end thereof, and a predetermined length, and wherein said central lumen is coextensive with said inflation segment.

6. The medical sealing device of claim 5, wherein said conduit and said inflation segment comprise a unitary structure constructed of a homogeneous substance.

7. The medical sealing device of claim 5, further comprising an atraumatic extension disposed at an outward end of said inflation segment opposite its point of connection with said conduit, said atraumatic extension being constructed of a flexible material.

8. The medical sealing device of claim 7, wherein said conduit, said inflation segment, and said atraumatic extension comprise a unitary structure constructed of a homogeneous substance.

9. The medical sealing device of claim 1, wherein said expandable member has a tubular configuration in an uninflated state with a tube wall and opposing tube ends, said tube ends being sealingly secured to said inflation segment.

10. The medical sealing device of claim 9, wherein said expandable member has a rounded configuration in an inflated state.

11. The medical sealing device of claim 9, wherein said expandable member is a pneumatic member which is inflatable via a gas.

12. The medical sealing device of claim 1, wherein:
   i) said inflation segment is coaxially disposed from conduit distal end, and wherein said central lumen is coextensive with said extension member;
   ii) said expandable member has a tubular configuration in an uninflated state with a tube wall and opposing tube ends, said tube ends being sealingly secured to said inflation segment; and
   iii) said expandable member has a rounded configuration in an inflated state.

13. The medical sealing device of claim 1, wherein said apparatus is useable with a hemostatic valve introducer to seal a percutaneous puncture in the vascular system of a patient body, said conduit distal end being insertable through said introducer and the percutaneous puncture, said expandable member being first uninflated, said expandable member then being inflated, said conduit being slightly retracted to abut said expandable member against the percutaneous puncture, said introducer being removed from the percutaneous puncture, and said means to apply a tensive force engaging said conduit until patient body aperture closure.

14. A medical sealing apparatus for closing a percutaneous puncture in a patient's vascular system and for use with a hemostatic introducer, comprising:
   a. a thin, elongated conduit having a predetermined outside diameter and a central lumen, said conduit having proximal and distal ends, said conduit distal end being insertable into the patient body aperture and having an inflation segment including an external orifice which is communicatively connected to said lumen, said inflation segment coaxially extending from conduit distal end, said conduit proximal end having cylindrical outside configuration of the same diameter as that of said conduit:
   b. a hollow, inflatable member sealingly disposed at said conduit distal end inflation segment, said member being inflatable to a predetermined diameter, said member having a tubular configuration in an uninflated state with a tube wall and opposing tube ends, said tube ends being sealingly secured to said inflation segment, and said member having a rounded configuration in an inflated state;
   c. a seal adhereingly disposed within said conduit central lumen along a predetermined segment at said proximal end thereof, said seal consisting of a continuous, homogeneous packing of elastomeric material, said seal permitting sealing ingress and egress of a syringe to inject or evacuate a fluid into or from said conduit lumen for inflation and deflation of said inflatable member; and
   d. a fixation member for securement of said conduit in a fixed position on the patient body exterior, said fixation member having a base portion for contact with the patient body and means to engage said conduit.

15. A method for closing a percutaneous puncture in a patient's vascular system and which is insertable and removable through a standard, hemostatic sheath, comprising the steps of:
   a. providing a medical sealing apparatus, comprising:
      i) a thin, elongated conduit having a central lumen, said conduit having proximal and distal ends, said conduit distal end being insertable into the patient body aperture and having an inflation segment including an external orifice which is communicatively connected to said lumen, said conduit proximal end having a cylindrical outside configuration of a uniform diameter;
      ii. a hollow, inflatable member sealingly disposed at said conduit distal end inflation segment, said member being inflatable to a predetermined diameter;
      iii. a seal consisting of an elastomeric material continuously and adhereingly disposed in said conduit central lumen along a predetermined segment at said proximal end thereof, said seal permitting ingress and egress of fluid to and from said conduit lumen via a syringe; and
      iv. a securement member for fixing the position of the conduit on the patient body exterior, said securement member having a base portion for contact with the patient body and means to engage said conduit;
   b. inserting said apparatus through the sheath and into the percutaneous puncture;
   c. inflating said inflatable member by inserting a syringe through said elastomeric seal and injecting fluid into said central lumen;
   d. positioning said inflatable member into contact with the patient's vasculature;
   e. withdrawing the sheath longitudinally over said conduit; and
   f. securing said conduit in a fixed position at the patient body exterior via said fixation member.

16. A medical sealing apparatus for closing of an aperture in a patient body, comprising:
   a. a thin, elongated conduit having a central lumen, said conduit having proximal and distal ends, said conduit distal end being insertable into the patient body aperture and having an inflation segment including an external orifice which is communicatively connected to said lumen, said conduit proximal end having a cylindrical configuration of a uniform outside diameter;
   b. an expandable member sealingly disposed at said conduit distal end inflation segment, said expandable member being inflatable to a predetermined diameter;
   c. a seal consisting of an elastomeric material continuously and adhereingly disposed in said conduit central lumen along a predetermined segment at said proximal end thereof, said seal permitting ingress and egress of fluid to and from said conduit lumen via a syringe; and
   d. means to apply a longitudinally oriented tension force on the exterior of a patient body, with respect to said conduit central axis, to said expandable member when in an inserted, inflated state, whereby said expandable member is held in a stable position internal to the patient body aperture until the patient body aperture is closed.

* * * * *